United States Patent [19]

Chamberlin, Sr.

[11] Patent Number: Plant 6,200

[45] Date of Patent: Jun. 14, 1988

[54] PLUM TREE, "SCARLET SUN"

[75] Inventor: Thomas O. Chamberlin, Sr., Visalia, Calif.

[73] Assignee: Metzler Investments and Company, Del Rey, Calif.

[21] Appl. No.: 863,996

[22] Filed: May 16, 1986

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Roysum Plum Tree (U.S. Plant Pat. No. 2,619) from which it was derived as a sport, but from which it is distinguished by producing a fruit which ripens several weeks earlier than the Roysum Plum Tree and which is not self-fruiting and has a flesh which is a moderate orange-yellow in color and has a distinctive flavor.

1 Drawing Sheet

BACKGROUND OF THE NEW VARIETY

The present invention relates to a plum tree, designated varietally as "Scarlet Sun" and which is somewhat similar to the Roysum Plum Tree (U.S. Plant Pat. No. 2,619), from which it was derived as a sport, but from which it is distinguished by producing very large, bright red plums having a harvest date of approximately August 20 at Del Rey, Calif., and has pleasant tasting, moderate orange-yellow colored flesh and which further exhibits excellent cold storage and handling characteristics.

As manager of a large deciduous fruit company, the applicant is constantly on the alert to locate new and novel varieties of fruit for the purposes of improving the various produce that is sent to market from his employer's farms. During the performance of his routine duties, in the fall of 1977, the applicant discovered in a cultivated area, and subsequently marked what appeared to be a sport limb of a Roysum Plum Tree (U.S. Plant Pat. No. 2,619) bearing new and novel fruit at his employer's Ranch No. 28 located near Tulare, Calif. Budwood from the sport limb was taken, during the winter of 1977 and 1978, and grafted onto seedling test trees in the orchard located near Del Rey, Calif., to which reference has already been made. These test seedlings were thereafter observed and the first fruit of the subject variety was harvested in 1979. The applicant noted at the time that the test seedlings produced plums which were of a unique color and of a harvest date expected to be advantageous to his employer. As a consequence, more budwood was collected from these test trees for further asexual reproduction.

ORIGIN AND ASEXUAL REPRODUCTION OF THE NEW VARIETY

In the winter of 1979, budwood collected from the test seedlings was budded onto new test seedlings in the test plot. These new test trees were observed and the first fruit was borne by them in the summer of 1981. The applicant's various observations of these seedlings has lead him to conclude that the instant variety is probably not self-fruiting and therefore another plum tree is required to aid in the pollination of the "Scarlet Sun" Plum Tree. The budded seedlings have been continuously observed by the applicant and have proved to be identical in characteristics to those displayed by the original sport limb.

BRIEF DESCRIPTION OF THE DRAWING

The accompanying drawing is a color photograph of a characteristic twig bearing typical leaves, several plums showing their external coloration sufficiently matured for harvesting and shipment, and a plum halved transversely of the suture plane to illustrate the flesh coloration, and stone characteristics.

DETAILED DESCRIPTION

Referring more particularly to the pomological details of this new and distinct variety of plum tree, the following has been observed under the ecological conditions prevailing in the designated orchards near Del Rey, Calif. All major color code designations are by reference to the Inter-Society Color Council, National Bureau of Standards. Common descriptive color names are also used occasionally where deemed appropriate.

TREE

Size: Average.

Vigor: Vigorous.

Figure: Normal, with upright growth.

Productivity: Good, providing other plum trees that will aid in pollination are present.

Regularity of bearing: Good, provided that the trees selected to aid in pollination are appropriate.

Trunk:

- *Thickness.*—Average.
- *Texture.*—Normal plum bark.
- *Color.*—Brown, (61 gy. Br.).
- *Lenticels — number.*—Approximately 18 to 21 per square inch.
- *Lenticels — color.*—Light Brown, (76 L.Y.Br.).
- *Lenticels — size.*—Approximately ⅛ inch, (3.175 mm.).

Branches:

- *Size.*—Average.
- *Texture.*—The same surface texture as the trunk.
- *Color.*—Brown, (61 gy. Br.).
- *Lenticels — number.*—Approximately 18 to 21 per square inch.
- *Lenticels — size.*—Average in length, approximately ⅛ inch (3.175 mm.).
- *Lenticels — color.*—Light Brown, (76 L. Y. Br.).

LEAVES

Size: Medium to large.

*Length.*—Approximately 3½ to 4½ inches, (88.9 through 114.3 mm.).

*Width.*—Approximately 1½ to 2 inches, (38.1 through 50.8 mm.).

*Shape.*—Lanceolate.

*Color — dorsal surface.*—Green (127 gy. 01. G.).

*Color — ventral surface.*—Pale Green (122 g.y. G.).

*Marginal form.*—Crenate.

*Glands.*—None observed.

*Petiole — length.*—Approximately 11/16 inch, (17.462 mm.).

*Petiole — thickness.*—Approximately 1/16 inch, (1.588 mm.).

*Stem glands.*—None observed.

*Stipules.*—One pair may be found at the base of the petiole, however, they are very small. Size — approximately 5/16 inch in length, (7.938 mm.).

Flower buds:

*Size — length.*—Approximately 3/16 inch, (4.762 mm.).

*Size — diameter.*—Approximately ¼ inch, (6.350 mm.).

*Shape.*—Slightly elongated.

*Petiole.*—Length — approximately 3/16 inch, (4.762 mm.).

*Other characteristics.*—The buds of the instant variety develop separately.

*Color.*—Light Green (115 v. Y. G.).

Flowers:

*Date of bloom.*—Late February, or approximately nine days after the Santa Rosa Plum Tree (unpatented), at Del Rey, Calif.

*Petal size.*—Length — approximately 3/16 inch, (4.762 mm.).

*Petal size.*—Diameter — approximately ¼ inch, (6.350 mm.).

*Shape.*—Slightly elongated.

*Color.*—White (263 White).

*Petiole.*—Length — approximately ⅜ inch, (9.525 mm.).

FRUIT

Maturity when described: Mature for harvesting, approximately Aug. 20 at Del Rey, Calif.

Size:

*Generally.*—Large.

*Uniformity.*—Good.

*Axial diameter.*—Approximately 2-5/16 inches to 2⅝ inches, (58.738 through 66.675 mm.).

*Diameter transverse in the suture plane.*—Approximately 2-1/16 inches to 2½ inches, (52.388 through 63.5 mm.).

*Diameter transverse in the cheek plane.*—Approximately 2-5/16 inches to 2⅝ inches (58.738 through 66.675 mm.).

Form:

*Uniformity.*—Good.

*Shape.*—Most of the fruit of the subject variety appears to be somewhat slightly elongated.

Suture:

*Appearance.*—Very smooth.

*Length.*—Approximately 3½ inches to 3¾ inches, (88.9 through 95.250 mm.).

Ventral surfaces: Rounded, with a blunt apex.

Stem cavity:

*Shape.*—Round; very slightly elongated; approximately ⅛ inch to 3/16 inch deep, (approximately 3.175 through 4.762 mm.).

Base: Medium in width, and flat.

Apex: Slightly elongated, however, it is heavy and blunt.

Pistil point: Quite blunt.

Stem:

*Length.*—Approximately ⅜ inch, (9.525 mm.).

*Thickness.*—Approximately 1/16 inch, (1.588 mm.).

Skin:

*Thickness.*—Approximately the same as other plum varieties, approximately 1/64 inch or less, (0.397 mm.).

*Texture.*—Slightly rough.

*Tendency to crack.*—None observed.

*Color.*—Deep Bright Red (13 deep red).

Flesh:

*Color.*—Moderate Orange-Yellow (71 m. oy.).

*Texture of pit well.*—Slightly rough.

*Color of pit well.*—Dark Orange-Yellow, (72 d.oy.).

*Juice production.*—Medium juicy.

*Flavor.*—Noteworthy; the juice has a hint of tartness, however, it is quite pleasant as compared with other varieties.

*Aroma.*—Slight.

*Texture.*—Smooth and crisp.

*Fibers.*—None evident.

*Ripening.*—Even.

*Eating quality.*—Noteworthy.

Stone:

*Free or cling.*—Freestone.

*Fibers.*—None evident.

*Size.*—Length — approximately ¾ inch, (19.050 mm.). Width — approximately 9/16 inch, (14.288 mm.). Thickness — approximately 5/16 inch, (7.938 mm.).

*Form.*—Elongated.

*Color.*—Light Brown, (72 d. Oy.).

*Base.*—Small; there appears to be a flat area at the base.

*Sides.*—Slightly rough; no ridges are apparent.

Use: Fresh market.

Keeping quality: Excellent, the subject variety has been tested in cold storage for periods up to and including three weeks with no deleterious effects noted.

Shipping quality: The subject variety appears to have excellent shipping characteristics staying firm for extended periods of time in cold storage.

Although the new variety of plum tree possesses the described characteristics as a result of the growing conditions in Del Rey, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is new and desired to be secured by Plant Letters Patent is:

1. A new and distinct variety of plum tree substantially as illustrated and described which is somewhat similar to the Roysum Plum Tree (U.S. Plant Pat. No. 2,619) from which it was derived as a sport, but from which it is distinguished by bearing a bright red, quite large plum which ripens for harvesting several weeks before the Roysum Plum Tree, about August 20, at Del Rey, Calif., and which is further distinguished from the Roysum Plum Tree by being not self-fruiting and having a moderate orange-yellow colored flesh and a distinctive flavor.

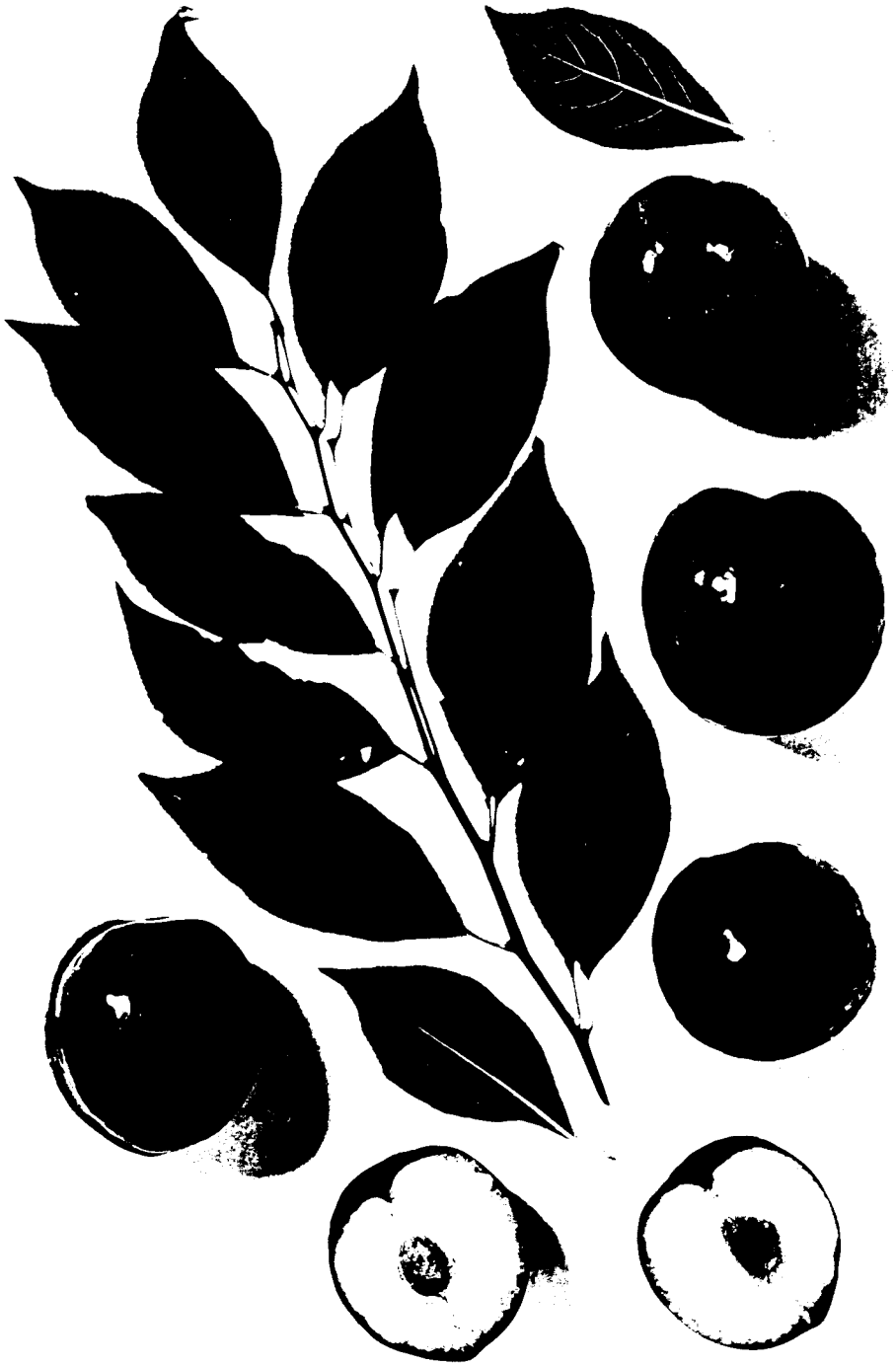

* * * * *